Oct. 13, 1953 S. F. HAHN Plant Pat. 1,221
SANSEVIERIA PLANT
Filed Aug. 15, 1952
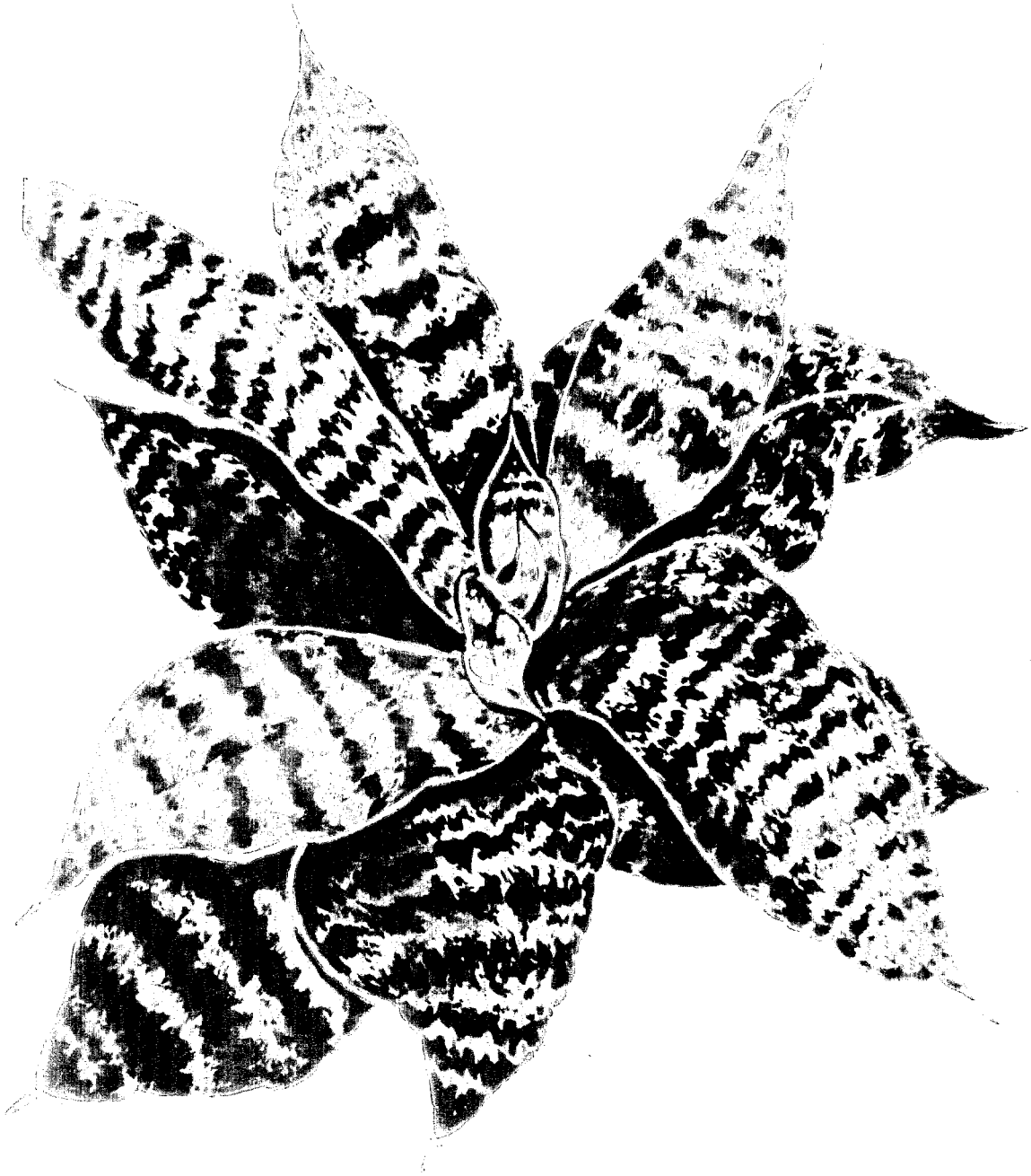
INVENTOR
Sylvan Frank Hahn
By Orville M. Kile
Plant Pat. Agent Patented Oct. 13, 1953

Plant Pat. 1,221

UNITED STATES PATENT OFFICE 1,221

SANSEVIERIA PLANT

Sylvan Frank Hahn, Pittsburgh, Pa.

Application August 15, 1952, Serial No. 304,665

1 Claim. (Cl. 47—59)

My present discovery pertains to a new variety of sansevieria plant. This plant in its habit of spiral or rosette form of growth is identical to my variety which is the subject of United States Plant Patent No. 470, but the coloration of the foliage is so singularly different that it constitutes a readily distinguishable and useful new variety. Whereas the coloration and markings of the foliage in Plant Patent No. 470 are typically that of the *Sansevieria zeylonica*, my new plant possesses a pure white to very pale yellow coloration along the entire length of the margin of the leaf blade.

This new variety is a sport of the subject of Plant Patent No. 470, known in the trade as Sansevieria Hahnii. It was discovered by me in my greenhouses located in New Orleans, Louisiana.

The variety has been asexually reproduced true to type by suckers (stonoliferous rhizomes which arise from adventitious buds), by me at my greenhouses located in New Orleans, Louisiana. It will not reproduce true to type when propagated from leaf cuttings.

The illustration accompanying this application gives a view looking downward into the plant. It shows the leaf arrangement and shape as well as the typical foliage coloration as nearly as the artist can portray them, in a plant when two years old. It must be understood, however, that there will be some variation in coloration and markings as between individual specimens of this variety.

In the following detailed description of this new variety, ordinary dictionary color terms are used except where color plates are cited, and such plate references are to Ridgway's Color Standards and Nomenclature.

Growth:

*Type.*—Compact, flat spiral or rosette; base of plant narrow and thin.

*Rapidity.*—Grows and reproduces rapidly and with ease.

*Size.*—Original plant has attained a size of 18 inches in height after several years' growth.

Leaves:

*Shape.*—Much broader and shorter than other known varieties, except the subject of Plant Patent No. 470 and sports therefrom. Narrow-ovate; very short-pointed on older leaves. Young leaves concave; older leaves flat.

*Size.*—Average size 12 centimeters long by 6 centimeters broad through the center.

*Margin.*—Entire; somewhat undulating.

*Color.*—The color of the leaf, with a notable exception set forth below, is the same as that of the subject of Plant Patent No. 470; that is, it has approximately the same coloration as the variety *Sansevieria zeylonica*—transverse irregular bands of dark green alternate with bands of lighter green and even silvery gray, these bands being roughly 7 millimeters broad. But this new plant has a distinct and novel feature in the coloration of the leaf margin. The color of the margin varies from a translucent white to pale yellow (Pale Calcedony Yellow, plate XVII). The size of this color band along the leaf margin varies in size from one thirty-second of one inch to nearly one quarter of one inch in width, the wider margin being exceptional.

*Position.*—Spreading from base; upper one-third horizontal to slightly reflexed.

*Base.*—Narrow.

Flowers: No flowers or fruit have ever been observed, although when the plants grow much older they may have such characters.

Having thus disclosed my discovery, I claim:

A new and distinct variety of sansevieria plant of the spiral or rosette type, substantially as shown and described, characterized particularly by its narrow band of white to pale yellow coloration along the leaf margin, and its habit of faithfully reproducing this novel feature only when propagated by using suckers.

SYLVAN FRANK HAHN.

No references cited.